United States Patent [19]

Wakao et al.

[11] Patent Number: 5,760,091

[45] Date of Patent: Jun. 2, 1998

[54] PREVENTIVE AGENTS AGAINST ADHESION OF MARINE ORGANISMS AND METHODS OF PREVENTING SUCH ADHESION OF MARINE ORGANISMS

[75] Inventors: Yoshiharu Wakao, Toyonaka; Toru Yasunaga, Osaka, both of Japan

[73] Assignee: Katayama Chemical, Inc., Osaka, Japan

[21] Appl. No.: 619,919

[22] Filed: Mar. 20, 1996

[30] Foreign Application Priority Data

Mar. 24, 1995 [JP] Japan .................................. 7-066342

[51] Int. Cl.$^6$ .................................................. A01N 33/02
[52] U.S. Cl. .......................... 514/663; 514/671; 514/673; 514/674
[58] Field of Search ................... 564/511, 512, 564/509, 463; 514/663, 671, 673, 674

[56] References Cited

FOREIGN PATENT DOCUMENTS

| | | |
|---|---|---|
| 56-003842 | 1/1981 | Japan . |
| 59-020641 | 5/1984 | Japan . |
| 60-023641 | 6/1985 | Japan . |
| 60-052726 | 11/1985 | Japan . |
| 1-197407 | 8/1989 | Japan . |
| 441403 | 2/1992 | Japan . |

OTHER PUBLICATIONS

Patent Abstracts of Japan, PN 56003842, 1981.
Patent Abstracts of Japan, PN 59020641, 1984.
Patent Abstracts of Japan, PN 6023641, 1985.
Patent Abstracts of Japan, PN 60052726, 1985.
Patent Abstracts of Japan, PN 1197407, 1989.
Patent Abstracts of Japan, PN 4041403, 1992.

*Primary Examiner*—Deborah Lambkin
*Attorney, Agent, or Firm*—Greenblum & Bernstein, P.L.C.

[57] ABSTRACT

A preventive agent against adhesion of a marine organism comprising: at least one amine compound represented by the following formula (I):

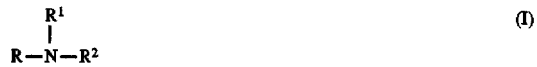

, wherein R is a $C_{8-22}$ saturated or unsaturated aliphatic hydrocarbon group, $R^1$ is hydrogen atom, aminopropyl, a $C_{1-22}$ saturated aliphatic hydrocarbon or $C_{2-22}$ unsaturated aliphatic hydrocarbon group, $R^2$ is aminopropyl, a $C_{1-8}$ saturated aliphatic hydrocarbon or $C_{2-8}$ unsaturated aliphatic hydrocarbon group, provided that $R^1$ is hydrogen atom or aminopropyl group when $R^2$ is represents aminopropyl group, or a salt thereof; and at least one N-alkyl polyamine compound represented by the following formula (II):

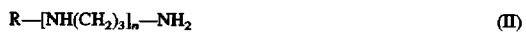

, wherein R is a $C_{8-22}$ saturated or unsaturated aliphatic hydrocarbon group and n is an integer from 2 to 4, or a salt thereof in an amount of 0.1 to 9 parts by weight to one part by weight of the compound (I).

15 Claims, No Drawings

PREVENTIVE AGENTS AGAINST ADHESION OF MARINE ORGANISMS AND METHODS OF PREVENTING SUCH ADHESION OF MARINE ORGANISMS

BACKGROUND OF THE INVENTION

1. Field of the Invention

The present invention relates to preventive agents against adhesion of marine organisms and methods to prevent such adhesion. Particularly, the preventive agents and methods can effectively protect seawater-drawing pipes, fishing nets, bottoms of ships and structures in the sea against fouling caused by marine organisms, especially serpulidae, by applying the agents to articles or structures, or adding them into seawater systems.

2. Description of Related Art

Recently, an increasing number of marine organisms, especially serpulidae, have been observed adhering in semi-closed bays and maricultures. In some factories using seawater as cooling water, they adhere to the insides of tubes of heat exchangers, causing pitting or corrosion. In some maricultures, they sometimes do great damage to oyster farm; and they sometimes adhere in a large number to culture fish crawl nets, obstruct a flow of seawater, cause dissolved oxygen to become in short supply in the crawls, resulting in death of bred fishes. When they adhere to the bottom of a ship, they reduce speed of the ship, giving such trouble that the ship must be docked for removal of them.

Conventionally, for protecting such seawater pipes, ships and fishing nets, a chlorine-base agent and an antifouling agent containing an organic tin compound or cuprous oxide were generally used. Since such compounds was toxic to marine organisms, serpulidae were prevented together with barnacles and mussels of *Mytilus edulis galloprovinciais*, *Perna viridis* and the like. However, because these antifouling agents containing metal are slow in degrading in the environment and also accumulates into organisms, use thereof has been restricted for preserving the environment. Therefore, development of an alternative safe antifouling agent is highly anticipated. As safety of compounds has been pursued, it has been obvious that the difference in effects of the agents on individual marine adherent organisms.

From the above point of view, higher aliphatic amine compounds have been proposed as safe preventive agents against adhesion of marine organisms (see Japanese Patent Publications Nos. SHO 56(1981)-3842, SHO 59(1984)-20641, SHO 60(1985)-23641, SHO 60(1985)-52726 and Japanese Unexamined Patent Publications Nos. HEI 1(1989)-197407 and HEI 4(1992)-41403).

The higher aliphatic amine compound as a safe preventive agent against marine adherent organisms is known to have potent effects of preventing adhesion of mussels of *Mytilus edulis galloprovinciais*, and barnacles. However, when used to prevent adhesion of serpulidae, it must be poured into a seawater system at a high concentration and, when used as antifouling agent, it must disperse from antifouling coating at a high concentration. That may cause environmental contamination and also is not preferable from economical viewpoint.

Serpulidae are marine adherent organisms belonging to Serpulidae family of Polychaeta class of *Annelida phylum* on the classification system. Their larvae swim in the sea and, when they touch suitable attached bases, they adhere to them, where they grow forming calcareous tubes with secretion. Sometimes such tubes grow to be more than 10 cm in thickness for about 2 months. Therefore, the serpulidae are considered to be one of the marine adherent organisms which cannot be removed easily.

SUMMARY OF THE INVENTION

The present invention, in view of the above circumstances, is to provide a preventive agent effective against adhesion of serpulidae which is harmless to man, animals, fishes and shellfishes, and is unlikely to contaminate the environment, and to provide a preventive method using the same. The preventive agent and method can be used on a fishing nets, water pipes and other structures in the sea area where adhesion of serpulidae is particularly observed.

The inventors, by having keen study on preventive agents effective against adhesion of serpulidae which hardly affect the environment, have found that combined use of at least two kinds of amine compounds in a remarkably small amount outperforms by comparison with single use of an individual amine compound in preventing the adhesion, and also have found the combined use prevents adhesion of other marine organisms in a similar amount.

The present invention, based on the above findings, provides a preventive agent against adhesion of a marine organism comprising:

at least one amine compound represented by the following formula (I):

, wherein R is a $C_{8-22}$ saturated or unsaturated aliphatic hydrocarbon group, $R^1$ is hydrogen atom, aminopropyl, a $C_{1-22}$ saturated aliphatic hydrocarbon or $C_{2-22}$ unsaturated aliphatic hydrocarbon group, $R^2$ is aminopropyl, a $C_{1-8}$ saturated aliphatic hydrocarbon or $C_{2-8}$ unsaturated aliphatic hydrocarbon group, provided that R' is hydrogen atom or aminopropyl group when $R^2$ is aminopropyl group, or a salt thereof; and at least one N-alkyl polyamine compound represented by the following formula (II):

, wherein R is a $C_{8-22}$ saturated or unsaturated aliphatic hydrocarbon group and n is an integer from 2 to 4, or a salt thereof in an amount of 0.1 to 9 parts by weight to one part by weight of the compound (I).

Further, the present invention provides a method of preventing adhesion of a marine organism comprising a simultaneous or separate adding to an objective seawater system subjected to antifouling of at least one amine compound (I) or a salt thereof and at least one N-alkyl polyamine compound (II) or a salt thereof at a concentration of 0.001 to 0.2 mg/L of seawater as the active ingredient.

The active ingredients of the invention are considered to have the following mechanism of preventing the adhesion: The amine compound of the formula (I) as well as the N-alkyl-polyamine compound of the formula (II), when existing individually, is readily adsorbed by an anion component such as suspended matter in water. Therefore, it cannot keep its dispersed state so that it does not act on target marine adherent organisms. However, simultaneous existence of these two compounds inhibits the adsorption and keeps the dispersed state, working effectively on marine adherent organisms such as serpulidae. Thus the ability to prevent the adhesion is enhanced.

DESCRIPTION OF THE PREFERRED EMBODIMENTS

The marine adherent organisms according to the invention includes serpulidae, barnacles, mussels such as *Mytilus edulis galloprovinciais, Perna viridis* and the like. Especially the serpulidae.

The objective system in seawater according to the invention includes 1) seawater aqueducts such as cooling seawater tubes in iron manufacturing factories, 2) fishing nets and facilities in maricultures, and 3) structures in the sea such as the bottoms of ships and bridges.

The compounds represented by the formulae (I) and (II) which are active ingredients of the invention are known, for which commercially available products may be used.

Preferred class of the compounds (I) is represented by the sub-formula (I'):

, wherein R is the same as defined in the formula (I) and R' is hydrogen atom or aminopropyl group.

Other preferred class of the compounds (I) is represented by the sub-formula (I"):

, wherein R is the same as defined in the formula (I), $R_a$ is a $C_{1-22}$ saturated aliphatic hydrocarbon or $C_{2-22}$ unsaturated aliphatic hydrocarbon group, and $R_b$ is a $C_{1-8}$ saturated aliphatic hydrocarbon or $C_{2-8}$ unsaturated aliphatic hydrocarbon group. The compound or compounds belonging to either one or both of these two classes may be used.

Examples of the $C_{8-22}$ saturated or unsaturated aliphatic hydrocarbon groups represented by R in the formulae (I) and (II) are alkyl groups such as octyl, decyl, dodecyl, hexadecyl and octadecyl, and alkenyl groups such as oleyl, coconut alkyl, beef tallow alkyl, hardened beef tallow alkyl and soybean alkyl.

Examples of the $C_{1-22}$ saturated aliphatic hydrocarbon groups represented by $R^1$ in the formula (I) or by $R_a$ in the sub-formula (I') are methyl, ethyl, propyl, butyl, pentyl, hexyl, octyl, decyl, dodecyl, tetradecyl, hexadecyl, octadecyl, coconut alkyl, beef tallow alkyl, hardened beef tallow alkyl and soybean alkyl.

Examples of the $C_{2-22}$ unsaturated aliphatic hydrocarbon group represented by $R^1$ or $R_a$ are vinyl, propenyl, butenyl, pentenyl, hexenyl, myristeyl, palmiteyl, oleyl, linoleyl, coconut alkyl, beef tallow alkyl, hardened beef tallow alkyl and soybean alkyl.

Examples of the $C_{1-8}$ saturated aliphatic hydrocarbon group represented by $R^2$ of the formula (I) or by $R_b$ of the sub-formula (I") are methyl, ethyl, propyl, butyl, pentyl, hexyl and octyl. Examples of the $C_{2-8}$ unsaturated aliphatic hydrocarbon groups represented by the same symbols are vinyl, propenyl, butenyl, pentenyl, hexenyl and octenyl. The above-mentioned alkyl groups include all the isomers thereof.

The coconut alkyl, beef tallow alkyl, hardened beef tallow alkyl and soybean alkyl groups here are $C_{12-20}$ saturated or unsaturated straight or branched chain aliphatic hydrocarbon groups produced with a known process from coconut oil or coconut fat, beef tallow and soybean oil respectively.

Specific examples of the compounds of the formula, especially those of the sub-formula (I') are N-dodecylpropylenediamine, N-hexadecyl-propylenediamine, N-octadecyl-propylenediamine, N-oleyl-propylenediamine, N-coconut alkyl-propylenediamine, N-beef tallow alkyl-propylenediamine, N-hardened beef tallow alkyl-propylenediamine, N-dodecyl-N,N-bis(3-aminopropyl)amine, N-hexadecyl-N,N-bis(3-aminopropyl)amine, N-octadecyl-N,N-bis(3-aminopropyl)amine, N-oleyl-N,N-bis(3-aminopropyl)amine, N-coconut alkyl-N,N-bis(3-aminopropyl)amine, N-beef tallow alkyl-N,N-bis(3-aminopropyl)amine and N-hardened beef tallow alkyl-N,N-bis(3-aminopropyl)amine, or salts thereof.

Specific examples of the compounds of the sub-formula (I") for the formula (I) are dodecyldimethylamine, tetradecyldimethylamine, hexadecyldimethylamine, octadecyldimethylamine, oleyldimethylamine, soybean alkyl dimethylamine, beef tallow alkyl dimethylamine, coconut alkyl dimethylamine, didodecylmethylamine, ditetradecylmethylamine, dihexadecylmethylamine, dioctadecylmethylamine, di(beef tallow alkyl)methylamine, di(coconut alkyl)methylamine, dodecyltetradecylmethylamine, dodecylhexadecylmethylamine, dodecyloctadecylmethylamine, tetradecylhexadecylmethylamine, tetradecyloctadecylmethylamine, hexadecyloctadecylmethylamine, dodecylmethylpropylamine, hexadecylmethylethylamine, beef tallow alkyl ethylpropylamine, beef tallow alkyl diethylamine, beef tallow alkyl dipropylamine, beef tallow alkyl methylhexylamine, coconut alkyl dipentylamine and coconut alkyl dihexylamine, or salts thereof.

Specific examples of the compounds of the formula (II) are N-dedecyl-dipropylenetriamine, N-hexadecyl-dipropylenetriamine, N-octadecyl-dipropylenetriamine, N-oleyl-dipropylenetriamine, N-coconut alkyl dipropylenetriamine, N-beef tallow alkyl-dipropylenetriamine, N-hardened beef tallow alkyl-dipropylenetriamine, N-dodecyl-tripropylenetetraamine, N-hexadecyl-tripropylenetetraamine, N-octadecyl-tripropylenetetraamine, N-oleyl-tripropylenetetraamine, N-coconut alkyl-tripropylenetetraamine, N-beef tallow alkyl-tripropylenetetraamine, N-hardened beef alkyl-tripropylenetetraamine, N-tetradecyl-tetrapropylenepentaamine, N-coconut alkyl-tetrapropylenepentaamine, N-hexadecyl-tetrapropylenepentaamine, N-octadecyl-tetrapropylenepentaamine and N-beef tallow alkyl-tetrapropylenepentaamine, or salts thereof.

Usable acids for forming these salts are inorganic acids such as hydrochloric, hydrobromic, nitric, sulfuric or phosphoric acid; organic acids such as formic, acetic, oleic, naphthenic, adipic, lactic, citric or benzoic acid, and anionic residues of saccharin.

The preventive agent against adhesion of marine organisms of the present invention comprises a combination of the compound of the formula (I) and the compound of the formula (II). Preferable examples of the combination are as follows:

(1) The combination of the compound of the formula (I), especially the sub-formula (I'), and the compound of the formula (II) are N-coconut alkyl propylenediamine and N-beef tallow alkyl-tripropylenetetraamine, N-beef tallow alkyl propylenediamine and N-oleyl-tripropylenetetraamine, N-hexadecyl-propylenediamine and N-octadecyl-dipropylenetriamine, N-beef tallow alkyl-N,N-bis(3-aminopropyl)amine and N-dodecyl-tripropylenetetraamine, N-octadecylpropylenediamine and N-coconut alkyl-dipropylenetriamine, N-hexadecylpropylenediamine and N-beef tallow alkyl-dipropylenetriamine, N-beef tallow alkyl-propylenediamine and N-dodecyl-tripropylenetetraamine, N-coconut alkyl propylenediamine and N-hexadecyl-tripropylenetetraamine, N-beef alkyl-N,N-bis(3-aminopropyl)amine and N-coconut alkyl-dipropylenetriamine, N-oleyl-propylenediamine and N-beef tallow alkyl-dipropylenetriamine, N-oleyl-propylenediamine and N-beef tallow alkyl-tetrapropylenepentaamine, N-oleyl-N,N-bis(3-aminopropyl)amine and N-beef tallow alkyl-tetrapropylenepentaamine, and N-coconut alkyl-propylenediamine and N-beef tallow alkyl-tetrapropylenepentaamine.

(2) The combinations of the compound of the formula (I), especially the sub-formula (I"), and the compound of the formula (II) are dodecyldimethylamine and N-coconut alkyl-dipropylenetriamine, beef tallow alkyl dimethylamine and N-dodecyl-tripropylenetetraamine, oleyldimethylamine and N-beef tallow alkyl-dipropylenetriamine, hexadecyldimethylamine and N-oleyl-tripropylenetetraamine, and soybean alkyl dimethylamine and N-octadecyl-tetrapropylenepentaamine.

(3) The combinations of the compound of the formula (I), especially the compounds of the sub-formula (I') and the sub-formula (I"), with the compound of the formula (II) are N-oleyl-propylenediamine and didodecylmethylamine with N-coconut alkyl-dipropylenetriamine, N-beef tallow alkyl-N,N-bis(3-aminopropyl)amine and soybean alkyl dimethylamine with N-octadecyl-tripropylenetetraamine, N-dodecylpropylenediamine and oleyldimethylamine with N-tetradecyltetrapropylenepentaamine, N-hexadecyl-propylenediamine and beef tallow alkyl-dimethylamine with N-hexadecyl-dipropylenetriamine, N-coconut alkyl-N,N-bis(3-aminopropyl)amine and oleyldimethylamine with N-octadecyl-tripropylenetetraamine, N-soybean alkyl-N,N-bis(3-aminopropyl)amine and oleyldimethylamine with N-beef tallow alkyl-tripropylenetetraamine, and N-dodecyl-propylenediamine and tetradecylhexadecylmethylamine with N-tetradecyl-tetrapropylenepentaamine.

Alternatively, the respective salts of the above amines or at least one of them may be used in the combination.

The preventive agent against adhesion of marine organisms according to the invention contains the compound of the formula (II) at a ratio from 0.1 to 9 parts by weight, preferable from 0.2 to 8 parts by weight, with respect to 1 part by weight of the compound of the formula (I).

When the compounds of the sub-formulae (I') and (I") are used together as the compound of the formula (I), they are preferably contained at a weight ratio from 1:10 to 10:1 for antifouling and antifoaming.

The compound of the sub-formula (I"), particularly, has the ability to inhibit foaming which results from the compounds of the formula (I') and (II), or from the compound of the formula (II), and therefore is suitable to use on a preventive object system wherein foaming may cause trouble.

Preferably, the preventive agent against adhesion of marine organisms of the invention is usually prepared in a liquid formulation, but not limited thereto depending on an object for which it is used.

When the objective system is a cooling seawater system, the preventive agent is preferably in the form of an aqueous formulation. Such a formulation can be prepared using a conventional method by mixing the active ingredients of the invention with water or a hydrophilic organic solvent and, if necessary, adding a surfactant.

Examples of the hydrophilic organic solvents are ethanol, propanol, isopropanol, butyl diglycol, ethylene glycol and propylene glycol monomethyl ether. These hydrophilic organic solvents may be used as a mixture with water.

Examples of the surfactants are polyoxyethylene alkyl ethers, polyoxyethylene alkyl esters, polyoxyethylene sorbitan alkyl esters, polyoxyethylene polyoxypropylene copolymer and alkylbetaines.

When used for a fishing net or the like, the preventive agent is preferably prepared in a liquid-type formulation. That is, the active ingredients of the invention are prepared by a conventional method into the antifouling agent by using an organic solvent as a medium and optionally adding a film-forming agent, plasticizer, coloring agent and the like.

Examples of the above organic solvents are ethanol, butanol, xylene, toluene, kerosene, methylisobutylketone, butyl acetate, naphtha and propylene glycol monomethyl ether. Other various solvents which are used for paints may be used. A little amount of water can also be contained.

Examples of the film-forming agents such as natural or synthetic resins are rosin resin, coumarone resin, polybutene, polyvinyl chloride, polybutyral and acrylic resin. Examples of the plasticizers are liquid paraffin, nonylphenol, dioctyl phthalate, diadipate phthalate and trioctyl phosphate.

It is preferred that the antifouling agent used for fishing net contains 10 to 30 wt % active ingredients, 3 to 30 wt % film-forming agent, 0 to 10 wt % plasticizer and an organic solvent at the remaining percentage with the whole solid concentration being 25 to 60 wt %, considering the film-formation and strength of the film.

The antifouling agent is used for fishing net by dipping or coating.

Further, when used for the bottom of a ship or a structure in the sea, the preventive agent may be prepared into a antifouling coating by further adding pigments to the above antifouling agent for fishing net.

Examples of the pigments are talc, titanium white, chrome yellow, Prussian blue, red oxide and phthalocyanine blue.

The antifouling coating may contain 10 to 30 wt % of the active ingredients, 3 to 25 wt % of the film-forming agent, 0 to 10 wt % of the plasticizer and 10 to 30 wt % of the pigment.

The antifouling coating is aptly applied to various marine structures by brushing, spraying and the like. The preventive agent of the invention thus applied exhibits long-term effects with antifouling film being formed with drying.

The antifouling active ingredients of the invention may be optionally used as a mixture with a known antifouling agent such as copper naphthenate, copper oleate, dimethyldithiocarbamate, tetraethyluram disulfide, zinc pyrithione, 2,3-dichloro-N-(2',6'-diethylphenyl)maleimide and 4,5-dichloro-2-n-octylisothiazolin-3-one.

The method of preventing adhesion of marine organisms according to the invention is as mentioned above.

In the method of the invention, the above-described active ingredients, when simultaneously added, are more easily used in a single formation, but the effects are the same when they are separately added. Also in this case, they are preferably prepared into a formation suitable for use as described above.

In the method of the invention, the addition amount of the active ingredients may vary depending on the objective seawater systems, but is usually sufficient at a concentration of about 0.001 to about 0.2mg/L of seawater, preferably about 0.003 to about 0.1 mg/L.

The active ingredients, when used for a cooling seawater system in particular, are poured for 12 to 24 hours per day in the above addition amount with respect to a flow rate of seawater, with good effects. The addition amount may slightly vary according to states of the sea water, and is preferably increased when a lot of serpulidae grow. However, the concentration up to 0.5 mg/L of seawater may be sufficient in any condition, and the concentration exceeding the limit is not preferred from an environmental and economical point of view.

In the method of the invention, other known antifouling agents may be used together as previously described.

The present invention will be hereinafter described in detail with reference to the following formulation examples, test examples and comparative examples, but these examples are not to be construed to limit the scope of the invention.

FORMULATION EXAMPLES

The formulations of the invention were made into emulsion or water-soluble type. For the emulsion type, the amine compounds were dissolved in isopropyl alcohol, to which Toxanon P-900 (Trademark, manufactured by Sanyo Chem. Ind., Ltd., Japan, nonionic and anionic surfactant HLB>12) was added for emulsifying. For the water-soluble type, the amine compounds were equimolecularly reacted with hydrochloric acid, acetic acid or other organic acid to form aqueous formulation.

| Formulation 1 (Table 1, Example 1) | |
|---|---|
| N-Coconut alkyl-propylenediamine | 15% |
| N-Beef tallow alkyl-tripropylenetetraamine | 15% |
| Hydrochloric acid | 9% |
| Isopropyl alcohol | 10% |
| Water | 51% |
| Formulation 2 (Table 1, Example 2) | |
| N-Beef tallow alkyl-propylenediamine | 25% |
| N-Oleyl-tripropylenetetraamine | 5% |
| Acetic acid | 2.5% |
| Toxanon P-900 (HLB > 12) | 25% |
| Diethyleneglycol monomethyl ether | 42.5% |
| Formulation 3 (Table 1, Example 3) | |
| N-Hexadecyl-propylenediamine | 20% |
| N-Octadecyl-dipropylenetriamine | 10% |
| Toxanon P-900 (HLB > 12) | 30% |
| Diethyleneglycol monomethyl ether | 40% |
| Formulation 4 (Table 2, Example 7) | |
| Dodecyldimethylamine | 25% |
| N-Coconut alkyl-dipropylenetriamine | 5% |
| Acetic acid | 10% |
| Isopropyl alcohol | 10% |
| Water | 50% |
| Formulation 5 (Table 2, Example 8) | |
| N-Beef tallow alkyl-dimethylamine | 5% |
| N-Dodecyl-tripropylenetetraamine | 25% |
| Lactic acid | 23% |
| Toxanon P-900 | 7% |
| Diethyleneglycol monomethyl ether | 40% |
| Formulation 6 (Table 2, Example 9) | |
| N-Oleyl-propylenediamine | 10% |
| Didodecylmethylamine | 10% |
| N-Coconut alkyl-dipropylenetriamine | 4% |
| Acetic acid | 2% |
| Toxanon P-900 | 18% |
| Diethyleneglycol monomethyl ether | 56% |
| Formulation 7 (Table 2, Example 10) | |
| N-Beef tallow alkyl-N,N-bis(3-aminopropyl)amine | 10% |
| Soybean alkyldimethylamine | 3% |
| N-Octadecyl-tripropylenetetraamine | 10% |
| Toxanon P-900 | 25% |
| Diethylene glycol monomethyl ether | 52% |
| Formulation Example 8 (Table 3, Comparative Example 2) | |
| N-Beef tallow alkyl-N,N-bis(3-aminopropyl)amine | 20% |
| Toxanon P-900 | 20% |
| Diethyleneglycol monomethyl ether | 60% |

Test Example 1

(Test on preventive effects against adhesion in a seawater system)

Seawater was pumped with a submersible pump from a seawater conduit in an iron manufacturing factory where serpulidae, caused a lot of trouble, and was passed in one direction through model passageways of PVC (polyvinyl chloride) tube with inner diameters of 65 mm and lengths of 2 m with test nets put therein (at a flow rate of 2 tons/hour) for 40 days in the adhering season of serpulidae. Into the passageways, each the formulation prepared, as the above mentioned were poured with chemical pumps. Then the number of serpulidae and other organisms which adhered was counted. The injected chemicals and are shown in Tables 1 to 4 (Tables 1 and 3 are the results testing from June to August in 1994 and Tables 2 and 4 are the results testing from June to August in 1995), wherein the following symbols denote respective chemicals:

(1) Compounds of the sub-formula (I')
    I'-a: N-Dodecyl-propylenediamine
    I'-b: N-Hexadecyl-propylenediamine
    I'-c: N-Octadecyl-propylenediamine
    I'-d: N-Oleyl-propylenediamine
    I'-e: N-Coconut alkyl-propylenediamine
    I'-f: N-Beef tallow alkyl-propylenediamine
    I'-g: N-Hardened beef tallow alkyl-propylenediamine
    I'-h: N-Beef tallow alkyl-N,N-bis(3-aminopropyl)amine
    I'-i: N-Hardened beef tallow alkyl-N,N-bis(3-aminopropyl)amine
    I'-j: N-Soybean alkyl-N,N-bis(3-aminopropyl)amine
    I'-k: N-Oleyl-N,N-bis(3-aminopropyl)amine (2) Compounds of the sub-formula (I")
    I"-a: Dodecyldimethylamine
    I"-b: Oleyldimethylamine
    I"-c: Soybean alkyl dimethylamine
    I"-d: Beef tallow alkyl dimethylamine
    I"-e: Didodecylmethylamine
    I"-f: Tetradecylhexadecylmethylamine (3) Compounds of the formula (II)
    II-a: N-Octadecyl-dipropylenetriamine
    II-b: N-Coconut alkyl-dipropylenetriamine
    II-c: N-Dodecyl-tripropylenetetraamine
    II-d: N-Octadecyl-tripropylenetetraamine
    II-e: N-Oleyl-tripropylenetetraamine
    II-f: N-Beef tallow alkyl-tripropylenetetraamine
    II-g: N-Beef tallow alkyl-tetrapropylenepentaamine
    II-h: N-Tetradecyl-tetrapropylenepentaamine
    II-i: N-Hexadecyl-tripropylenetetraamine
    II-j: N-Beef tallow alkyl-dipropylenetriamine (4) Other component
    III-a: Zinc dimethyldithiocarbamate

TABLE 1

| Examples | Compound.Salt | Concentration (mg/l) | Dosing Time (Hr) | Ratio | Serpulidae Adhered number (number /m²) | Serpulidae Mean length of tube (mm) | Barnacles Adhered number (number /m²) | Barnacles Mean major axis of base (mm) | Green Mussels Adhered number (number /m²) | Green Mussels Mean length of shell (mm) | Tubularia coverage (%) |
|---|---|---|---|---|---|---|---|---|---|---|---|
| 1 | I'-e.hydrochloride | 0.01 | 24 | 1.0 | 0 | — | 300 | <1 | 0 | — | 0 |
|   | II-f.hydrochloride | 0.01 |   | 1.0 |   |   |   |   |   |   |   |
| 2 | I'-f | 0.02 | 24 | 1.0 | 0 | — | 200 | <1 | 0 | — | 0 |
|   | II-e.acetate | 0.004 |   | 0.2 |   |   |   |   |   |   |   |
| 3 | I'-b | 0.03 | 18 | 1.0 | 0 | — | 300 | <1 | 0 | — | 0 |
|   | II-a | 0.015 |   | 0.5 |   |   |   |   |   |   |   |
| 4 | I'-h | 0.005 | 14 | 1.0 | 0 | — | 500 | <1 | 0 | — | 0 |
|   | II-c.lactate | 0.04 |   | 8.0 |   |   |   |   |   |   |   |
| 5 | I'-c.citrate | 0.005 | 24 | 1.0 | 0 | — | 100 | <1 | 0 | — | 0 |
|   | II-b | 0.025 |   | 5.0 |   |   |   |   |   |   |   |
| 6 | I'-d | 0.005 | 24 | 1.0 | 0 | — | 200 | <1 | 0 | — | 0 |
|   | II-g | 0.02 |   | 4.0 |   |   |   |   |   |   |   |

TABLE 2

| Examples | Compound.Salt | Concentration (mg/l) | Dosing Time (Hr) | Ratio | Serpulidae Adhered number (number /m²) | Serpulidae Mean length of tube (mm) | Barnacles Adhered number (number /m²) | Barnacles Mean major axis of base (mm) | Green Mussels Adhered number (number /m²) | Green Mussels Mean length of shell (mm) | Tubularia coverage (%) |
|---|---|---|---|---|---|---|---|---|---|---|---|
| 7 | I''-a.acetate | 0.05 | 18 | 1.0 | 0 | — | 50 | <1 | 0 | — | 0 |
|   | II-b.acetate | 0.01 |   | 0.2 |   |   |   |   |   |   |   |
| 8 | I''-d | 0.008 | 24 | 1.0 | 0 | — | 10 | <1 | 0 | — | 0 |
|   | II-c.lactate | 0.04 |   | 5.0 |   |   |   |   |   |   |   |
| 9 | I'-d | 0.04 | 20 | 1.0 | 0 | — | 20 | <1 | 0 | — | 0 |
|   | I''-e.acetate | 0.04 |   | 1.0 |   |   |   |   |   |   |   |
|   | II-b | 0.016 |   | 0.4 |   |   |   |   |   |   |   |
| 10 | I'-h | 0.02 | 24 | 1.0 | 0 | — | 10 | <1 | 0 | — | 0 |
|   | I''-c | 0.006 |   | 0.3 |   |   |   |   |   |   |   |
|   | II-d | 0.02 |   | 1.0 |   |   |   |   |   |   |   |
| 11 | I'-a.hydrochloride | 0.006 | 20 | 1.0 | 0 | — | 10 | <1 | 0 | — | 0 |
|   | I''-b | 0.03 |   | 5.0 |   |   |   |   |   |   |   |
|   | II-h.citrate | 0.03 |   | 5.0 |   |   |   |   |   |   |   |

TABLE 3

| Comparative Examples | Compound.Salt | Concentration (mg/l) | Dosing Time (Hr) | Serpulidae Adhered number (number /m²) | Serpulidae Mean length of tube (mm) | Barnacles Adhered number (number /m²) | Barnacles Mean major axis of base (mm) | Green Mussels Adhered number (number /m²) | Green Mussels Mean length of shell (mm) | Tubularia coverage (%) |
|---|---|---|---|---|---|---|---|---|---|---|
| 1 | I'-f.hydrochloride | 0.08 | 24 | 28000 | 10 | 1500 | 1 | 1500 | 1 | 10 |
| 2 | I'-h | 0.10 | 18 | 25000 | 11 | 5000 | 2 | 3000 | 1 | 15 |
| 3 | II-b.acetate | 0.06 | 24 | 12000 | 10 | 3000 | 2 | 2000 | 1 | 10 |
| 4 | II-e | 0.04 | 14 | 15000 | 10 | 3000 | <1 | 2000 | 1 | 15 |
| 5 | II-g | 0.06 | 24 | 17000 | 10 | 4000 | 2 | 2000 | 1 | 15 |
| 6 | Untreated | — | — | 58000 | 14 | 43000 | 9 | 32000 | 8 | 45 |

TABLE 4

| Comparative Examples | Compound.Salt | Concentration (mg/l) | Dosing Time (Hr) | Serpulidae Adhered number (number /m²) | Serpulidae Mean length of tube (mm) | Barnacles Adhered number (number /m²) | Barnacles Mean major axis of base (mm) | Green Mussels Adhered number (number /m²) | Green Mussels Mean length of shell (mm) | Tubularia coverage (%) |
|---|---|---|---|---|---|---|---|---|---|---|
| 7 | I'-a.hydrochloride | 2.0 | 16 | 18000 | 12 | 200 | 4 | 900 | 1 | 15 |
| 8 | I"-b | 1.0 | 18 | 15000 | 12 | 100 | 1 | 500 | 1 | 5 |
| 9 | I"-c | 0.5 | 20 | 6000 | 10 | 100 | 1 | 1000 | 1 | 20 |
| 10 | I"-d | 0.05 | 24 | 2000 | 13 | 50 | 1 | 700 | 1 | 5 |
| 11 | I"-e.acetate | 0.08 | 24 | 5000 | 10 | 50 | 1 | 900 | 1 | 5 |
| 12 | I'-d | 1.0 | 18 | 13000 | 13 | 1500 | 3 | 2000 | 1 | 20 |
| 13 | II-d.hydrochloride | 0.5 | 24 | 10000 | 12 | 1200 | 2 | 1500 | 1 | 15 |
| 14 | Untreated | — | — | 62000 | 14 | 35000 | 11 | 26000 | 9 | 40 |

Consideration

From the above test results, combined use of the compound of the sub-formular (I') and/or the compound of the sub-formula (I") with the compound of the formula (II) was found to have a synergistic effect (see Ex. Nos. 1 to 11) against prevention of serpulidae adhesion, while single use of the individual compound did not exhibit effects against serpulidae (see Comp. Ex. Nos. 1 to 14).

Test Example 2

(Test on preventive effects against adhesion to fishing nets)

Culture nets made of polyethylene (100 strings, 5 knots, 40 cm×60 cm) were used as test nets. Antifouling agents for fishing nets were prepared at the mixing ratios shown in Table 5 to 7. The test nets were dipped into each of the antifouling agents to allow the agents to stick thereto, and then air-dried for 3 days. The test nets were then hung at a depth of 1.0 to 1.5 m from the surface of the sea from raft in Houzaura Bay, Mie Prefecture, Japan for 3 months from May through July. At the end of the period, the antifouling effects against serpulidae and other adherent organisms were observed. The results are shown in Table 8, wherein shown are the weight (wet weight) of adhering organisms and percentage by weight of the individual adhering organisms.

TABLE 5

| Examples | Compound.Salt | Ratio of solid content | Ratio | Dioctyl phthalate | Liquid paraffin | Acrylic resin | Polybutene | Rosin resin | Coumarone resin | PGM* | Xylene | Sum |
|---|---|---|---|---|---|---|---|---|---|---|---|---|
| 1' | I'-b.hydrochloride | 10.0 | 1.0 | 5 | | 10 | | 10 | | 10 | 45 | 100 |
| | II-j.hydrochloride | 10.0 | 1.0 | | | | | | | | | |
| 2' | I'-f | 2.3 | 1.0 | | 10 | 5 | 5 | 5 | 5 | 20 | 30 | 100 |
| | II-c.acetate | 17.7 | 7.7 | | | | | | | | | |
| 3' | I'-e | 16.7 | 1.0 | | 5 | 10 | | 5 | 5 | | 55 | 100 |
| | II-i | 3.3 | 0.2 | | | | | | | | | |
| 4' | I'-h | 6.7 | 1.0 | 5 | 5 | 10 | 5 | 5 | | 15 | 35 | 100 |
| | II-b.citrate | 13.3 | 2.0 | | | | | | | | | |
| 5' | I'-d.acetate | 4.0 | 1.0 | 5 | | 10 | 5 | | 5 | 10 | 45 | 100 |
| | II-j | 16.0 | 4.0 | | | | | | | | | |

*PGM: propylenegylcol monomethylether

TABLE 6

| Examples | Compound.Salt | Ratio of solid content | Ratio | Dioctyl phthalate | Liquid paraffin | Acrylic resin | Polybutene | Rosin resin | Coumarone resin | PGM* | Xylene | Sum |
|---|---|---|---|---|---|---|---|---|---|---|---|---|
| 6' | I'-e | 5.0 | 1.0 | 5 | | 10 | 5 | 5 | 5 | 5 | 45 | 100 |
| | II-g.acetate | 15.0 | 3.0 | | | | | | | | | |
| 7' | I'-g | 7.5 | 1.0 | 5 | 5 | 5 | 5 | 10 | | | 55 | 100 |
| | II-e | 7.5 | 1.0 | | | | | | | | | |
| | III-a | 5.0 | | | | | | | | | | |

TABLE 6-continued

| Examples | Compound.Salt | Ratio of solid content | Ratio | Mixing Ratio (parts by weight) | | | | | | | | |
|---|---|---|---|---|---|---|---|---|---|---|---|---|
| | | | | Dioctyl phthalate | Liquid paraffin | Acrylic resin | Polybutene | Rosin resin | Coumarone resin | PGM* | Xylene | Sum |
| 8' | I"-a.hydrochloride | 10.0 | 1.0 | | 5 | 10 | | 5 | 5 | | 55 | 100 |
| | II-a.hydrochloride | 10.0 | 1.0 | | | | | | | | | |
| 9' | I'-j | 10.0 | 1.0 | | 10 | 5 | 5 | 5 | | 15 | 40 | 100 |
| | I"-b.acetate | 5.0 | 0.5 | | | | | | | | | |
| | II-f | 5.0 | 0.5 | | | | | | | | | |
| 10' | I'-a.hydrochloride | 6.0 | 1.0 | 5 | | 10 | 5 | | 5 | 10 | 45 | 100 |
| | I"-f.acetate | 9.0 | 1.5 | | | | | | | | | |
| | II-h.hydrochloride | 5.0 | 0.8 | | | | | | | | | |

*PGM: propylenegylcol monomethylether

TABLE 7

| Comparative Examples | Compound.Salt | Ratio of solid content | Mixing Ratio (parts by weight) | | | | | | | | |
|---|---|---|---|---|---|---|---|---|---|---|---|
| | | | Dioctyl phthalate | Liquid paraffin | Acrylic resin | Polybutene | Rosin resin | Coumarone resin | PGM* | Xylene | Sum |
| 1' | I'-b.acetate | 20.0 | 5 | | 10 | 5 | 5 | | 10 | 45 | 100 |
| 2' | I'-g | 20.0 | 5 | 5 | 5 | 5 | 5 | 5 | | 50 | 100 |
| 3' | I'-h | 20.0 | 5 | | 10 | | 5 | 5 | | 55 | 100 |
| 4' | II-j | 20.0 | | 10 | | 5 | 10 | 5 | 5 | 45 | 100 |
| 5' | II-b.hydrochloride | 20.0 | 5 | | 10 | | 5 | 5 | 10 | 45 | 100 |
| 6' | II-e | 20.0 | 5 | | 10 | 5 | | 5 | | 55 | 100 |
| 7' | II-g.acetate | 20.0 | | 10 | | 5 | 10 | 5 | 5 | 45 | 100 |
| 8' | I"-a | 20.0 | 5 | | 10 | 5 | | 5 | | 55 | 100 |
| 9' | I"-f.hydrochloride | 20.0 | 5 | | 10 | 5 | 10 | | 5 | 45 | 100 |
| 10' | Untreated | — | — | — | — | — | — | — | — | — | — |

*PGM: propylenegylcol monomethylether

TABLE 8

| | Adhering organisms after 3 months: percentage (%) | | | | Wet weight (g) of adhering matters after 3 months |
|---|---|---|---|---|---|
| | Serpulidae | Barnacles | Blue Mussels | Polyzoa | |
| Examples | | | | | |
| 1' | 0 | 0 | 0 | 0 | 10 |
| 2' | 0 | 0 | 0 | 0 | 10 |
| 3' | 0 | 0 | 0 | 0 | 10 |
| 4' | 0 | 0 | 0 | 0 | 10 |
| 5' | 0 | 0 | 0 | 0 | 10 |
| 6' | 0 | 0 | 0 | 0 | 10 |
| 7' | 0 | 0 | 0 | 0 | 10 |
| 8' | 0 | 0 | 0 | 0 | 10 |
| 9' | 0 | 0 | 0 | 0 | 10 |
| 10' | 0 | 0 | 0 | 0 | 10 |
| Comparative Examples | | | | | |
| 1' | 60 | 20 | 0 | 20 | 520 |
| 2' | 70 | 20 | 0 | 10 | 400 |
| 3' | 40 | 30 | 10 | 20 | 600 |
| 4' | 60 | 20 | 0 | 20 | 450 |
| 5' | 50 | 30 | 10 | 10 | 550 |
| 6' | 60 | 10 | 0 | 30 | 390 |

TABLE 8-continued

|   | Adhering organisms after 3 months: percentage (%) | | | | Wet weight (g) of adhering matters after 3 months |
|---|---|---|---|---|---|
|   | Serpulidae | Barnacles | Blue Mussels | Polyzoa | |
| 7' | 60 | 20 | 5 | 15 | 500 |
| 8' | 60 | 20 | 10 | 10 | 400 |
| 9' | 70 | 10 | 10 | 10 | 430 |
| 10' | 60 | 10 | 10 | 20 | 2300 |

Consideration

From the above test results, it was found that the antifouling agents for fishing nets of the invention prepared by mixing the compound of the sub-formula (I') and/or the compound of the sub-formula (I") with the compound of the formula (II) exhibited antifouling effects against serpulidae for a long time more than 3 months (see Ex. Nos. 1' to 10'), while single use of the individual compound did not exhibit long-term effects (see Comp. Ex. Nos. 1 to 10').

Test Example 3

(Test on antifouling effects as antifouling coating)

Rigid PVC boards of 7 cm×20 cm were used as test boards. Antifouling paints were prepared at the mixing ratios shown in Table 9 to 11. Each paint was applied twice to the board in an amount from 1.5 to 2.0 kg/m². The test boards were then hung at a depth of 1.0 to 1.5 m from the surface of the sea from raft in Houzaura Bay, Mie Prefecture, Japan for a year from May. After 6 months and 12 months from the hanging, the antifouling effect against serpulidae and other adherent organisms was observed. The results are shown in Tables 12 and 13, wherein shown are the weight (wet weight) of adhering organisms and percentage by weight of individual adhering organisms.

TABLE 9

| Examples | Compound.Salt | Ratio of solid content | Ratio | Mixing Ratio (parts by weight) | | | | | | | | | | | | |
|---|---|---|---|---|---|---|---|---|---|---|---|---|---|---|---|---|
| | | | | Talc | Titanium white | Phthalocyanine-B | Red oxide | Dioctyl phthalate | Liquid paraffin | Acrylic resin | Polybutene | Rosin resin | Coumarone resin | PGM* | Xylene | Sum |
| 1" | I'-b.hydrochloride | 10.0 | 1.0 | | 10 | | 10 | 8 | | 10 | 5 | 5 | | 7 | 25 | 100 |
| | II-j.hydrochloride | 10.0 | 1.0 | | | | | | | | | | | | | |
| 2" | I'-f | 2.3 | 1.0 | 5 | 15 | 5 | | | 8 | 10 | | 5 | 5 | 5 | 22 | 100 |
| | II-c.acetate | 17.7 | 7.7 | | | | | | | | | | | | | |
| 3" | I'-e | 16.7 | 1.0 | | 20 | 3 | | 7 | | | 5 | 10 | 5 | | 30 | 100 |
| | II-i | 3.3 | 0.2 | | | | | | | | | | | | | |
| 4" | I'-h | 6.7 | 1.0 | | 5 | | 15 | 6 | | 10 | | 10 | | | 34 | 100 |
| | II-b.citrate | 13.3 | 2.0 | | | | | | | | | | | | | |
| 5" | I'-d.acetate | 4.0 | 1.0 | 10 | 10 | 3 | | | 8 | 10 | 5 | | 5 | 5 | 24 | 100 |
| | II-j | 16.0 | 4.0 | | | | | | | | | | | | | |
| 6" | I'-k | 16.0 | 1.0 | 3 | 5 | 5 | 10 | 8 | | 10 | 5 | 5 | 5 | | 24 | 100 |
| | II-g | 4.0 | 0.25 | | | | | | | | | | | | | |

*PGM: propyleneglycol monomethylether

TABLE 10

| Examples | Compound.Salt | Ratio of solid content | Ratio | Mixing Ratio (parts by weight) | | | | | | | | | | | | |
|---|---|---|---|---|---|---|---|---|---|---|---|---|---|---|---|---|
| | | | | Talc | Titanium white | Phthalocyanine-B | Red oxide | Dioctyl phthalate | Liquid paraffin | Acrylic resin | Polybutene | Rosin resin | Coumarone resin | PGM* | Xylene | Sum |
| 7" | I'-g | 7.5 | 1.0 | | 10 | | 10 | 3 | 7 | 10 | 10 | | | 5 | 30 | 100 |
| | II-e | 7.5 | 1.0 | | | | | | | | | | | | | |
| | III-a | 5.0 | | | | | | | | | | | | | | |
| 8" | I'-a.hydrochloride | 10.0 | 1.0 | | 10 | | 10 | 7 | | 15 | | 5 | 5 | | 28 | 100 |
| | II-a.hydrochloride | 10.0 | 1.0 | | | | | | | | | | | | | |
| 9" | I'-j | 10.0 | 1.0 | 5 | 15 | | | | 10 | 10 | 10 | | | 5 | 25 | 100 |

TABLE 10-continued

| Examples | Compound·Salt | Ratio of solid content | Ratio | Talc | Titanium white | Phthalocyanine-B | Red oxide | Dioctyl phthalate | Liquid paraffin | Acrylic resin | Polybutene | Rosin resin | Coumarone resin | PGM* | Xylene | Sum |
|---|---|---|---|---|---|---|---|---|---|---|---|---|---|---|---|---|
| | I"-b.acetate | 5.0 | 0.5 | | | | | | | | | | | | | |
| | II-f | 5.0 | 0.5 | | | | | | | | | | | | | |
| 10" | I'-a.hydrochloride | 6.0 | 1.0 | 15 | 3 | | | 7 | | 10 | | 10 | | | 35 | 100 |
| | I"-f.acetate | 9.0 | 1.5 | | | | | | | | | | | | | |
| | II-h.hydrochloride | 5.0 | 0.8 | | | | | | | | | | | | | |

*PGM: propylenegylcol monomethylether

TABLE 11

| Comparative Examples | Compound·Salt | Ratio of solid content | Talc | Titanium white | Phthalocyanine-B | Red oxide | Dioctyl phthalate | Liquid paraffin | Acrylic resin | Polybutene | Rosin resin | Coumarone resin | PGM* | Xylene | Sum |
|---|---|---|---|---|---|---|---|---|---|---|---|---|---|---|---|
| 1" | I'-b.acetate | 20.0 | 5 | 15 | 3 | | 6 | | 10 | | 5 | 5 | 5 | 26 | 100 |
| 2" | I'-g | 20.0 | | 7 | | 13 | 8 | | | 5 | | 10 | 7 | 30 | 100 |
| 3" | I'-h | 20.0 | 5 | 12 | 3 | | | 6 | 5 | 5 | 5 | 5 | | 34 | 100 |
| 4" | II-j | 20.0 | | 5 | | 15 | | 8 | 10 | | | 10 | | 32 | 100 |
| 5" | II-b.hydrochloride | 20.0 | 8 | 13 | | | 7 | | 5 | 5 | 5 | 5 | 2 | 30 | 100 |
| 6" | II-e | 20.0 | | 18 | 3 | | | 7 | | 10 | 5 | 5 | | 32 | 100 |
| 7" | II-g | 20.0 | | 10 | | 10 | 5 | | 5 | 5 | | 10 | | 35 | 100 |
| 8" | I"-a | 20.0 | | 8 | | 12 | 7 | | | 10 | 8 | | | 35 | 100 |
| 9" | I"-f.hydrochloride | 20.0 | 5 | 13 | | | 7 | 5 | 3 | 5 | 7 | | | 35 | 100 |
| 10" | Untreated | — | — | — | — | — | — | — | — | — | — | — | — | — | — |

*PGM: propylenegylcol monomethylether

TABLE 12

| | All adhering organisms after 6 months/all | Adhering organisms after 6 months: Adhered area (%) | | | | All adhering organisms after 12 months/all | Adhering organisms after 12 months: Adhered area (%) | | | |
|---|---|---|---|---|---|---|---|---|---|---|
| Examples | adhered area (%) | Serpulidae | Barnacles | Bivalves | Polyzoa | adhered area (%) | Serpulidae | Barnacles | Bivalves | Polyzoa |
| 1" | 0 | 0 | 0 | 0 | 0 | 25 | 0 | 10 | 0 | 15 |
| 2" | 0 | 0 | 0 | 0 | 0 | 20 | 0 | 5 | 5 | 10 |
| 3" | 0 | 0 | 0 | 0 | 0 | 20 | 0 | 0 | 10 | 10 |
| 4" | 0 | 0 | 0 | 0 | 0 | 25 | 0 | 10 | 5 | 10 |
| 5" | 0 | 0 | 0 | 0 | 0 | 20 | 0 | 0 | 10 | 10 |
| 6" | 0 | 0 | 0 | 0 | 0 | 20 | 0 | 5 | 5 | 10 |
| 7" | 0 | 0 | 0 | 0 | 0 | 20 | 0 | 10 | 0 | 10 |
| 8" | 0 | 0 | 0 | 0 | 0 | 20 | 0 | 5 | 0 | 15 |
| 9" | 0 | 0 | 0 | 0 | 0 | 20 | 0 | 5 | 5 | 10 |
| 10" | 0 | 0 | 0 | 0 | 0 | 20 | 0 | 10 | 0 | 10 |

TABLE 13

| Comparative Examples | All adhering organisms after 6 months/all adhered area (%) | Adhering organisms after 6 months: Adhered area (%) | | | | All adhering organisms after 12 months/all adhered area (%) | Adhering organisms after 12 months: Adhered area (%) | | | |
|---|---|---|---|---|---|---|---|---|---|---|
| | | Serpulidae | Barnacles | Bivalves | Polyzoa | | Serpulidae | Barnacles | Bivalves | Polyzoa |
| 1" | 50 | 30 | 10 | 0 | 10 | 100 | 50 | 20 | 10 | 20 |
| 2" | 60 | 40 | 0 | 10 | 10 | 100 | 60 | 10 | 10 | 20 |
| 3" | 60 | 20 | 20 | 10 | 10 | 100 | 45 | 30 | 10 | 15 |
| 4" | 40 | 20 | 0 | 10 | 10 | 100 | 50 | 10 | 25 | 15 |
| 5" | 50 | 20 | 0 | 15 | 15 | 100 | 50 | 10 | 15 | 25 |
| 6" | 40 | 20 | 0 | 10 | 10 | 100 | 45 | 15 | 15 | 25 |
| 7" | 60 | 30 | 10 | 10 | 10 | 100 | 55 | 15 | 15 | 15 |
| 8" | 50 | 20 | 10 | 10 | 10 | 100 | 45 | 30 | 5 | 20 |
| 9" | 60 | 30 | 20 | 5 | 5 | 100 | 50 | 25 | 10 | 15 |
| 10" | 100 | 60 | 20 | 10 | 10 | 100 | 40 | 30 | 10 | 20 |

Consideration

From the above test results, it was found that the antifouling agents of the invention prepared by mixing the compound of the sub-formula (I') and/or the compound of the sub-formula (I") with the compound of the formula (II) exhibited antifouling effects against serpulidae for a long time more than 6 months (see Ex. Nos. 1" to 10"), while single use of the individual compound did not exhibit long-term effects (see Comp. Ex. Nos. 1" to 10").

The antifouling agent for cooling seawater systems and fishing nets and antifouling paint according to the invention can efficiently avoid damage caused by marine adherent organisms, especially by serpulidae, for a long time more than 12 months.

What is claimed is:

1. A preventive agent against adhesion of a marine organism, comprising:

at least one amine compound or salt thereof represented by the following formula (I):

wherein R is selected from the group consisting of $C_{8-22}$ saturated aliphatic hydrocarbons and $C_{8-22}$ unsaturated aliphatic hydrocarbons, $R^1$ is selected from the group consisting of hydrogen, aminopropyl, $C_{1-22}$ saturated aliphatic hydrocarbons, and $C_{2-22}$ unsaturated aliphatic hydrocarbons, $R^2$ is selected from the group consisting of aminopropyl, $C_{1-8}$ saturated aliphatic hydrocarbons, and $C_{2-8}$ unsaturated aliphatic hydrocarbons, provided that $R^1$ is selected from the group consisting of hydrogen and aminopropyl when $R^2$ is aminopropyl, and at least one N-alkyl polyamine compound or salt thereof represented by the following formula (II):

wherein R is selected from the group consisting of $C_{8-22}$ saturated aliphatic hydrocarbons and $C_{8-22}$ unsaturated aliphatic hydrocarbons, and n is an integer from 2 to 4; and wherein the at least one compound (II) or salt thereof is present in a synergistically effective amount of 0.1 to 9 parts by weight to one part by weight of the at least one compound (I) or salt thereof.

2. The preventive agent against adhesion of a marine organism of claim 1, wherein $R^1$ is selected from the group consisting of hydrogen and aminopropyl and $R^2$ is —$(CH_2)_3$—$NH_2$.

3. The preventive agent against adhesion of a marine organism of claim 1, wherein $R^1$ is selected from the group consisting of $C_{1-22}$ saturated aliphatic hydrocarbons and $C_{2-22}$ unsaturated aliphatic hydrocarbons, and $R^2$ is selected from the group consisting of $C_{1-8}$ saturated aliphatic hydrocarbons and $C_{2-8}$ unsaturated aliphatic hydrocarbons.

4. The preventive agent against adhesion of a marine organism of claim 1, wherein the at least one amine compound or salt thereof of formula (I) includes:

a first compound or salt thereof wherein $R^1$ is selected from the group consisting of hydrogen and aminopropyl and $R^2$ is —$(CH_2)_3$—$NH_2$, and a second compound or salt thereof wherein $R^1$ is selected from the group consisting of $C_{1-22}$ saturated aliphatic hydrocarbons and $C_{2-22}$ unsaturated aliphatic hydrocarbons, and $R^2$ is selected from the group consisting of $C_{1-8}$ saturated aliphatic hydrocarbons and $C_{2-8}$ unsaturated aliphatic hydrocarbons; and wherein a weight ratio of the first compound or salt thereof to the second compound or salt thereof is from 1:10 to 10:1.

5. The preventive agent against adhesion of a marine organism of claim 1, wherein R is a $C_{8-22}$ saturated or unsaturated aliphatic hydrocarbon selected from the group consisting of octyl, decyl, dodecyl, tetradecyl, hexadecyl, octadecyl, oleyl, coconut alkyl, beef tallow alkyl, hardened beef tallow alkyl, and soybean alkyl.

6. The preventive agent against adhesion of a marine organism of claim 1, wherein $R^1$ is a $C_{1-22}$ saturated aliphatic hydrocarbon selected from the group consisting of methyl, ethyl, propyl, butyl, pentyl, hexyl, octyl, decyl, dodecyl, tetradecyl, hexadecyl, octadecyl, coconut alkyl, beef tallow alkyl, hardened beef tallow alkyl, and soybean alkyl.

7. The preventive agent against adhesion of a marine organism of claim 1 wherein $R^1$ is a $C_{2-22}$ unsaturated aliphatic hydrocarbon selected from the group consisting of myristeyl, palmiteyl, oleyl, linoleyl, coconut alkyl, beef tallow alkyl, hardened beef tallow alkyl, and soybean alkyl.

8. The preventive agent against adhesion of a marine organism of claim 2, wherein the at least one amine compound or salt thereof of formula (1) is selected from the group consisting of N-dodecyl-propylenediamine, N-hexadecyl-propylenediamine, N-octadecyl-propylenediamine, N-oleyl-propylenediamine, N-coconut alkyl-propylenediamine, N-beef tallow alkyl-propylenedianine, N-hardened beef tallow alkyl-propylenediamine, N-beef tallow alkyl-N,N-bis(3-aminopropyl)amine, N-hardened beef tallow alkyl-N,N-bis(3-aminopropyl)amine, N-soybean alkyl-N,N-bis(3-aminopropyl)-amine, and N-oleyl-N,N-bis-(3-aminopropyl)amine.

9. The preventive agent against adhesion of a marine organism of claim 3, wherein the at least one amine compound or salt thereof of formula (I) is selected from the group consisting of dodecyldimethylamine, oleyldimethylamine, soybean alkyl dimethylamine, beef tallow alkyl dimethylamine, didodecylmethylamine, and tetradecylhexadecylmethylamine.

10. The preventive agent against adhesion of a marine organism of claim 1, wherein the at least one N-alkyl polyamine compound or salt thereof of formula (II) is selected from the group consisting of N-octadecyl-dipropylenetriamine, N-coconut alkyl-dipropylenetriamine, N-dodecyl-tripropylenetetraamine, N-octadecyl-tripropylenetetraamine, N-oleyl-tripropylenetetraamine, N-beef tallow alkyl tripropylenetetraamine, N-beef tallow alkyl-tetrapropylenepentaamine, N-tetradecyl-tetrapropylenepentaamine, N-hexadecyl-tripropylenetetraamine, and N-beef tallow alkyl-dipropylenetriamine.

11. The preventive agent against adhesion of a marine organism of claim 1, wherein compound (II) or salt thereof is present in an amount of 0.2 to 8 parts by weight to one part by weight of compound (I) or salt thereof.

12. A method of preventing adhesion of a marine organism, comprising:

adding to a seawater system at least one amine compound or salt thereof represented by the following formula (I):

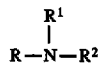

wherein R is selected from the group consisting of $C_{8-22}$ saturated aliphatic hydrocarbons and $C_{8-22}$ unsaturated aliphatic hydrocarbons, $R^1$ is selected from the group consisting of hydrogen, aminopropyl, $C_{1-22}$ saturated aliphatic hydrocarbons, and $C_{2-22}$ unsaturated aliphatic hydrocarbons, $R^2$ is selected from the group consisting of aminopropyl, $C_{1-8}$ saturated aliphatic hydrocarbons, and $C_{2-8}$ unsaturated aliphatic hydrocarbons, provided that $R^1$ is selected from the group consisting of hydrogen and aminopropyl when $R^2$ is aminopropyl;

adding to the seawater system at least one N-alkyl polyamine compound or salt thereof represented by the following formula (II):

$$R-\{NH(CH_2)_3\}_n-NH_2 \qquad (II)$$

wherein R is selected from the group consisting of $C_{8-22}$ saturated aliphatic hydrocarbons and $C_{8-22}$ unsaturated aliphatic hydrocarbons, and n is an integer from 2 to 4, in a synergistically effective amount of 0.1 to 9 parts by weight to one part by weight of the compound (I) or salt thereof; and wherein compound (I) or salt thereof and compound (II) or salt thereof are added to a combined concentration of about 0.001 to about 0.2 mg/L of seawater.

13. The method of claim 12, wherein compound (I) or salt thereof and compound (II) or salt thereof are simultaneously added to the seawater system.

14. The method of claim 12, wherein compound (I) or salt thereof and compound (II) or salt thereof are separately added to the seawater system.

15. The method of claim 12, wherein the marine organism comprises serpulidae.

* * * * *